United States Patent
Dickie et al.

(10) Patent No.: US 10,588,596 B2
(45) Date of Patent: Mar. 17, 2020

(54) SYSTEMS AND METHODS FOR DETECTING AND ENHANCING VIEWING OF A NEEDLE DURING ULTRASOUND IMAGING

(71) Applicant: Clarius Mobile Health Corp., Burnaby (CA)

(72) Inventors: Kris Dickie, Vancouver (CA); Nishant Uniyal, Vancouver (CA)

(73) Assignee: Clarius Mobile Health Corp., Burnaby, British Columbia (CA)

( * ) Notice: Subject to any disclaimer, the term of this patent is extended or adjusted under 35 U.S.C. 154(b) by 433 days.

(21) Appl. No.: 15/458,962

(22) Filed: Mar. 14, 2017

(65) Prior Publication Data
US 2018/0263593 A1 Sep. 20, 2018

(51) Int. Cl.
*A61B 8/00* (2006.01)
*A61B 8/08* (2006.01)
*A61B 8/14* (2006.01)

(52) U.S. Cl.
CPC .......... *A61B 8/0841* (2013.01); *A61B 8/5253* (2013.01); *A61B 8/54* (2013.01);
(Continued)

(58) Field of Classification Search
None
See application file for complete search history.

(56) References Cited

U.S. PATENT DOCUMENTS 5,501,223 A  3/1996 Washburn et al.
5,817,022 A * 10/1998 Vesely ............... G01S 15/87
600/443

(Continued)

FOREIGN PATENT DOCUMENTS

KR   101907550 B1 * 10/2018 .......... A61B 8/0841

OTHER PUBLICATIONS

Zhuang, B., Dickie, K., and Pelissier, L. "Adaptive spatial compounding for needle visualization." Ultrasonics Symposium (IUS), 2011 IEEE International. IEEE, 2011.

*Primary Examiner* — Joanne M Hoffman
(74) *Attorney, Agent, or Firm* — Julian Ho (57) ABSTRACT

The present embodiments relate generally to ultrasound imaging methods, systems, and apparatus that detect and enhance viewing of a needle during ultrasound imaging. The methods involve acquiring an ultrasound image feed having primary ultrasound image frames. During acquisition of the ultrasound image feed, secondary frames are interspersed amongst the primary ultrasound image frames, where each secondary frame is steered at a different angle. At least one secondary frame is analyzed to detect an imaged needle. Upon detection of an imaged needle in at least one secondary frame, an optimal steering angle is determined for imaging the needle, the optimal steering angle being based on the steered angle of the at least one secondary frame having the detected imaged needle. The method continues to acquire the ultrasound image feed by acquiring additional primary ultrasound image frames. During the continued acquisition of the ultrasound image feed, tertiary frames are interspersed amongst the additional primary ultrasound image frames, where each tertiary frame is steered at the optimal steering angle. The ultrasound image feed can then be displayed with enhanced viewing of the imaged needle, with the enhanced viewing being based on the interspersed tertiary frames.

16 Claims, 4 Drawing Sheets

(52) U.S. Cl.
CPC ............... *A61B 8/14* (2013.01); *A61B 8/4483* (2013.01); *A61B 8/461* (2013.01); *A61B 8/5215* (2013.01)

(56) References Cited

U.S. PATENT DOCUMENTS

| | | | |
|---|---|---|---|
| 6,048,312 A * | 4/2000 | Ishrak | A61B 8/0833 |
| | | | 128/916 |
| 6,221,020 B1 | 4/2001 | Lysyansky et al. | |
| 6,346,079 B1 | 2/2002 | Haider et al. | |
| 7,670,293 B2 | 3/2010 | Dubberstein et al. | |
| 7,775,981 B1 * | 8/2010 | Guracar | A61B 8/481 |
| | | | 600/447 |
| 8,343,054 B1 * | 1/2013 | Tamura | A61B 8/0841 |
| | | | 600/437 |
| 9,058,649 B2 | 6/2015 | Harrison et al. | |
| 9,324,155 B2 | 4/2016 | Mendonca et al. | |
| 9,386,964 B2 * | 7/2016 | Bagge | G01S 7/52068 |
| 2002/0173719 A1 * | 11/2002 | Zhao | A61B 8/0833 |
| | | | 600/437 |
| 2003/0065260 A1 * | 4/2003 | Cheng | A61B 8/0833 |
| | | | 600/427 |
| 2003/0097066 A1 * | 5/2003 | Shelby | A61B 8/0833 |
| | | | 600/443 |
| 2004/0106869 A1 * | 6/2004 | Tepper | A61B 8/0833 |
| | | | 600/443 |
| 2007/0078342 A1 * | 4/2007 | Jago | A61B 8/00 |
| | | | 600/443 |
| 2007/0081711 A1 * | 4/2007 | Kim | G06T 5/50 |
| | | | 382/128 |
| 2007/0167769 A1 * | 7/2007 | Ikuma | A61B 8/0833 |
| | | | 600/437 |
| 2008/0114240 A1 | 5/2008 | Sasaki | |
| 2008/0186378 A1 * | 8/2008 | Shen | A61B 8/0833 |
| | | | 348/65 |
| 2009/0171218 A1 * | 7/2009 | Nygaard | A61B 8/0833 |
| | | | 600/461 |
| 2010/0063393 A1 | 3/2010 | Moradi et al. | |
| 2010/0121189 A1 * | 5/2010 | Ma | A61B 8/00 |
| | | | 600/437 |
| 2010/0121190 A1 * | 5/2010 | Pagoulatos | A61B 8/00 |
| | | | 600/437 |
| 2010/0160783 A1 * | 6/2010 | Halmann | A61B 8/4281 |
| | | | 600/447 |
| 2010/0240997 A1 * | 9/2010 | Ichioka | A61B 8/00 |
| | | | 600/443 |
| 2012/0143055 A1 * | 6/2012 | Ng | A61B 8/0841 |
| | | | 600/439 |
| 2012/0209107 A1 * | 8/2012 | Guo | A61B 8/0841 |
| | | | 600/424 |
| 2013/0053687 A1 * | 2/2013 | Lin | A61B 8/0841 |
| | | | 600/424 |
| 2013/0253319 A1 | 9/2013 | Hamilton et al. | |
| 2014/0187945 A1 * | 7/2014 | Sandy | A61B 8/4477 |
| | | | 600/439 |
| 2014/0236001 A1 * | 8/2014 | Kondou | A61B 8/14 |
| | | | 600/424 |
| 2017/0143295 A1 * | 5/2017 | Park | A61B 8/0841 |
| 2018/0356493 A1 * | 12/2018 | Stapert | G01S 7/52026 |
| 2019/0201110 A1 * | 7/2019 | Kuenen | A61B 8/0841 |

\* cited by examiner

SYSTEMS AND METHODS FOR DETECTING AND ENHANCING VIEWING OF A NEEDLE DURING ULTRASOUND IMAGING

FIELD

The present disclosure relates generally to ultrasound imaging, and in particular, systems and methods for detecting and enhancing viewing of an imaged needle during ultrasound imaging.

BACKGROUND

Ultrasound imaging systems are a powerful tool for performing real-time imaging procedures in a wide range of medical applications. For example, in intervention procedures, needles are often used for administration of medicine or evacuation of fluid contents. Using ultrasound guidance while inserting a needle enhances the safety and efficacy of procedures by increasing the accuracy of the needle path to the target site.

A challenging part of using ultrasound to guide needle procedures is identifying the needle in an ultrasound image feed. For example, needles may be inserted into tissue at varying angles relative to the travel of the ultrasound signals used for imaging. When the ultrasound transmit signal is not perpendicular to the needle, the amount of reflected ultrasound signal that can be received by a transducer may be reduced significantly. This makes it difficult to obtain a clear image of the needle.

Different attempts have been made to address this drawback. In one traditional attempt, specialized needles are designed with microscopic ridges along their lengthwise surfaces to enhance echo reflections towards the transducer head. While these echogenically-enhanced needles improve needle visualization, they add cost for an ultrasound operator. Also, the use of echogenic needles may alter the typical workflow an operator is accustomed to if the operator normally uses non-echogenic needles for procedures.

There have been attempts to enhance imaging of regular needles. In some traditional systems, user input is required to identify an ultrasound beam steered angle for optimal needle imaging. This adds complexity to the user experience. Other traditional systems require less user input by cycling through a sequence of different steered angled frames to ensure a needle is imaged. However, such systems typically suffer from poor frame rate.

There is thus a need for improved systems and methods for detecting and enhancing viewing of a needle during ultrasound imaging. The embodiments discussed herein may address and/or ameliorate at least some of the aforementioned drawbacks identified above. The foregoing examples of the related art and limitations related thereto are intended to be illustrative and not exclusive. Other limitations of the related art will become apparent to those of skill in the art upon a reading of the specification and a study of the drawings herein.

BRIEF DESCRIPTION OF THE DRAWINGS

Non-limiting examples of various embodiments of the present disclosure will next be described in relation to the drawings, in which.

DETAILED DESCRIPTION

In a first broad aspect of the present disclosure, there is provided a method of ultrasound imaging, the method involving: acquiring an ultrasound image feed, the ultrasound image feed including primary ultrasound image frames; during acquisition of the ultrasound image feed, interspersing secondary frames amongst the primary ultrasound image frames, wherein each secondary frame is steered at a different angle; analyzing at least one secondary frame, of the interspersed secondary frames, to detect an imaged needle; upon detection of an imaged needle in the at least one secondary frame, determining an optimal steering angle for imaging the needle, the optimal steering angle being based on the steered angle of the at least one secondary frame having the detected imaged needle; continuing to acquire the ultrasound image feed by acquiring additional primary ultrasound image frames; and during the continued acquisition of the ultrasound image feed, interspersing tertiary frames amongst the additional primary ultrasound image frames, wherein each tertiary frame is steered at the optimal steering angle; and displaying the ultrasound image feed with enhanced viewing of the imaged needle, the enhanced viewing being based on the interspersed tertiary frames.

In some embodiments, upon commencement of the interspersing of tertiary frames, the method further involves ceasing the interspersing of secondary frames in the ultrasound image feed. In some embodiments, after a period of time, the method involves restoring the interspersing of secondary frames in the ultrasound image feed.

In some embodiments, during the continued acquisition of the ultrasound image feed, the method further involves: analyzing at least one tertiary frame, of the interspersed tertiary frames, to detect an absence of the imaged needle; and upon detection of the absence of the imaged needle in the at least one tertiary frame, restoring the interspersing of secondary frames in the ultrasound image feed.

In some embodiments, upon the restoring of the interspersing of secondary frames in the ultrasound image feed, the method further involves: ceasing the interspersing of tertiary frames in the ultrasound image feed; and ceasing the display of the ultrasound image feed with enhanced viewing of the imaged needle.

In some embodiments, the interspersing of secondary frames is performed by interleaving the secondary frames between successive primary ultrasound image frames.

In some embodiments, a frame rate of the ultrasound image feed, having the interspersed secondary frames amongst the plurality of ultrasound image frames, is maintained at least at 10 frames per second (fps).

In some embodiments, the primary ultrasound image frames are acquired using a first set of imaging parameters, and the interspersed secondary frames are acquired using a second set of imaging parameters; and the second set of imaging parameters result in the interspersed secondary frames having less image information than the primary ultrasound image frames. In some embodiments, the imaging parameters that are different between the first set of imaging parameters and the second set of imaging parameters is selected from a group consisting of: noise floor ratio, dynamic range, transmit frequency, receive frequency, line acquisition per transmit event, line density, and pulse width.

In some embodiments, the primary ultrasound image frames are acquired by transmitting ultrasound signals in a direction, and the interspersed secondary frames are steered on both sides of the direction. In some embodiments, the primary ultrasound image frames are acquired by transmitting ultrasound signals in a direction, and the interspersed secondary frames are steered at angles between ten (10) and sixty (60) degrees from the direction. In some embodiments, the interspersed secondary frames are successively steered in at least five (5) degree increments. In some embodiments, the interspersed secondary frames are successively steered in increments of no greater than twenty (20) degrees.

In some embodiments, when analyzing the at least one secondary frame, the needle is considered detected if the needle is determined to be imaged in at least two (2) successive secondary frames. In some embodiments, the optimal steering angle is determined by comparing the imaged needle in the at least two (2) successive secondary frames, and selecting the steered angle of the secondary frame having the optimal imaged needle.

In some embodiments, when analyzing the at least one tertiary frame, the needle is considered absent if the needle is determined to be not imaged in at least ten (10) successive tertiary frames. In some embodiments, when analyzing the at least one tertiary frame, the needle is considered absent if the needle is absent for at least one-third (⅓) of a second.

In some embodiments, the needle includes a needle not configured for enhanced echogenicity.

In another broad aspect of the present disclosure, there is provided an ultrasound imaging apparatus including: a processor; and a memory storing instructions for execution by the processor. When the instructions are executed by the processor, the processor is configured to: acquire an ultrasound image feed, the ultrasound image feed including primary ultrasound image frames; during acquisition of the ultrasound image feed, intersperse secondary frames amongst the primary ultrasound image frames, wherein each secondary frame is steered at a different angle; analyze at least one secondary frame, of the interspersed secondary frames, to detect an imaged needle; upon detection of an imaged needle in the at least one secondary frame, determine an optimal steering angle for imaging the needle, the optimal steering angle being based on the steered angle of the at least one secondary frame having the detected imaged needle; continue to acquire the ultrasound image feed by acquiring additional primary ultrasound image frames; and during the continued acquisition of the ultrasound image feed, intersperse tertiary frames amongst the additional primary ultrasound image frames, wherein each tertiary frame is steered at the optimal steering angle; and display the ultrasound image feed with enhanced viewing of the imaged needle, the enhanced viewing being based on the interspersed tertiary frames.

In another broad aspect of the present disclosure, there is provided a computer readable medium storing instructions for execution by a processor of an ultrasound imaging apparatus, wherein when the instructions are executed by the processor, the processor is configured to: acquire an ultrasound image feed, the ultrasound image feed including primary ultrasound image frames; during acquisition of the ultrasound image feed, intersperse secondary frames amongst the primary ultrasound image frames, wherein each secondary frame is steered at a different angle; analyze at least one secondary frame, of the interspersed secondary frames, to detect an imaged needle; upon detection of an imaged needle in the at least one secondary frame, determine an optimal steering angle for imaging the needle, the optimal steering angle being based on the steered angle of the at least one secondary frame having the detected imaged needle; continue to acquire the ultrasound image feed by acquiring additional primary ultrasound image frames; during the continued acquisition of the ultrasound image feed, intersperse tertiary frames amongst the additional primary ultrasound image frames, wherein each tertiary frame is steered at the optimal steering angle; and display the ultrasound image feed with enhanced viewing of the imaged needle, the enhanced viewing being based on the interspersed tertiary frames.

For simplicity and clarity of illustration, where considered appropriate, reference numerals may be repeated among the figures to indicate corresponding or analogous elements or steps. In addition, numerous specific details are set forth in order to provide a thorough understanding of the exemplary embodiments described herein. However, it will be understood by those of ordinary skill in the art that the embodiments described herein may be practiced without these specific details. In other instances, certain steps, signals, protocols, software, hardware, networking infrastructure, circuits, structures, techniques, well-known methods, procedures and components have not been described or shown in detail in order not to obscure the embodiments generally described herein.

Furthermore, this description is not to be considered as limiting the scope of the embodiments described herein in any way. It should be understood that the detailed description, while indicating specific embodiments, are given by way of illustration only, since various changes and modifications within the scope of the disclosure will become apparent to those skilled in the art from this detailed description. Accordingly, the specification and drawings are to be regarded in an illustrative, rather than a restrictive, sense.

Figure 1:
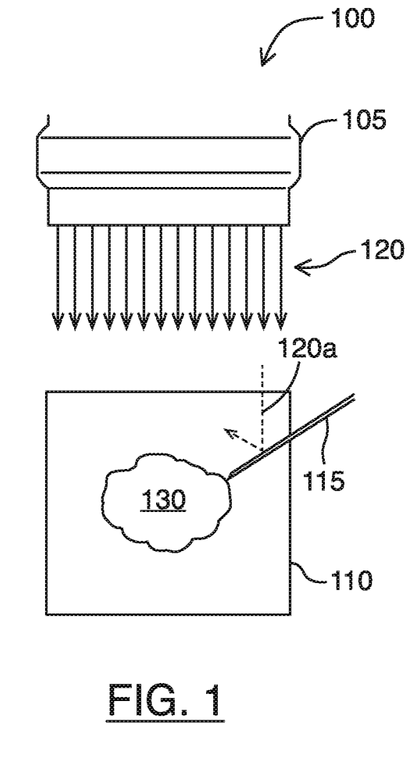
FIG. 1 is an illustration of traditional imaging using an ultrasound transducer and drawbacks when imaging a needle.

Referring to FIG. 1, shown there generally as 100 is an illustration of traditional imaging using an ultrasound transducer and drawbacks when imaging a needle. As illustrated, an ultrasound transducer 105 is typically placed against the skin of a patient. The ultrasound transducer 105 emits ultrasound signals 120 towards the tissue and corresponding echoes reflect off structures 130 (e.g., blood vessels, nerves, etc. depending on the medical application) to product an ultrasound image 110. In an intervention procedure, a needle 115 may be inserted into the surface of the skin towards the structure 130. Due to the insertion angle of the needle, the ultrasound signals 120a may reflect off of the needle at an angle that does not allow strong echo signals to be received at the transducer 105.

Figure 2:
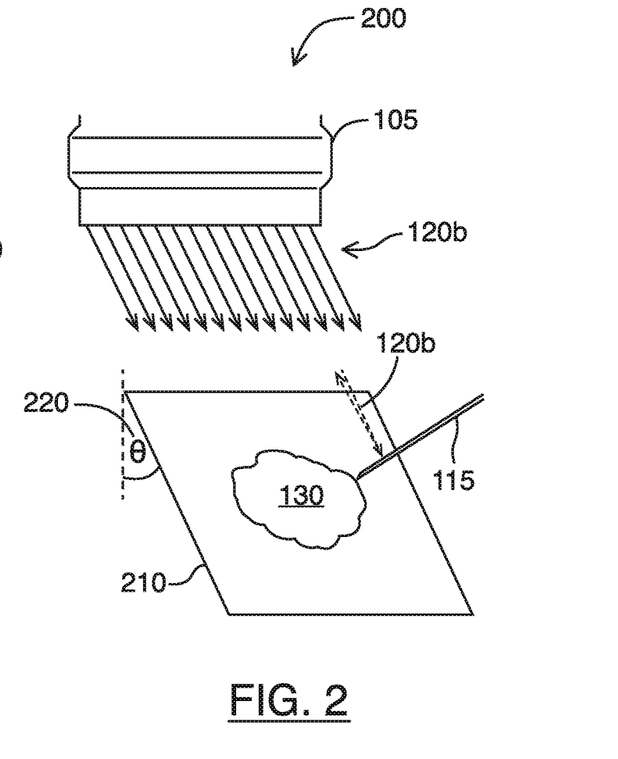
FIG. 2 is an illustration of how ultrasound signals can be steered to improve imaging of a needle.

Referring to FIG. 2, shown there generally as 200 is an illustration of how ultrasound signals can be steered to improve imaging of a needle. The transducer 105 may steer the ultrasound signals 120b so that they strike the needle 115 at an angle 220 that is at or close to normal to the length of the needle. The resultant angle of reflection will allow stronger echo signals be directed towards the transducer 105, to produce an steered ultrasound image 210 where the needle is more clearly shown.

While steering the ultrasound signals 120b may allow for optimal imaging of the needle, identifying the optimal steering angle for the ultrasound signals can present challenges. Some traditional systems require manual input of the angle at which the ultrasound signals should be steered. These systems allow for improved imaging of the needle, but they add complexity to the user experience. Other traditional systems sequentially cycle through a series of different angles in an attempt to image the needle regardless of the angle at which the needle is inserted. However, this configuration lowers the frame rate at which the tissues being imaged can be displayed. To minimize the impact on frame rate, these systems typically also limit the cycling of different angles to one side (left or right) of the transducer based on user input. Additional user input is thus also required in such systems to identify which side of the transducer the needle is being inserted on.

Figure 3:
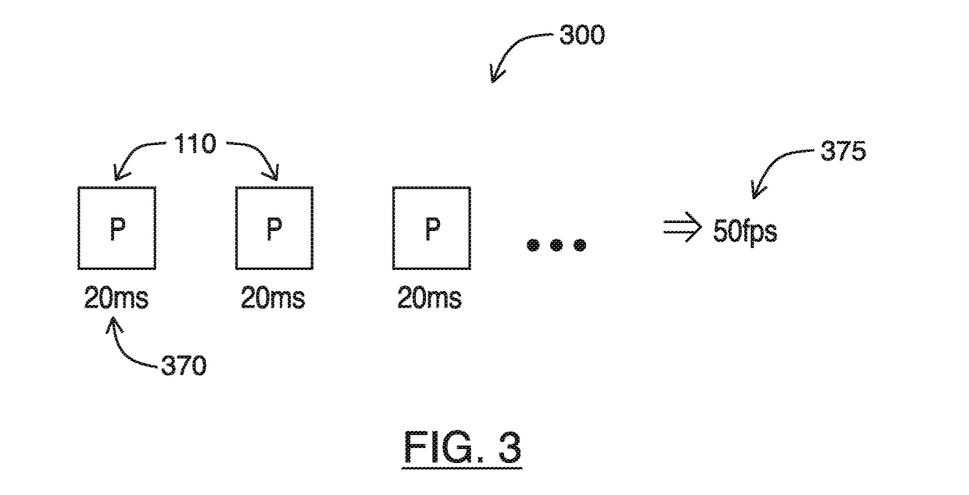
FIG. 3 shows a series of frames during traditional imaging and associated frame rates.

Referring to FIG. 3, shown there generally as 300 is a series of frames during traditional imaging, and associated frame rates. As shown, the frames may be ultrasound images 110 for imaging a structure 130 as shown in FIG. 1. These frames 110 constitute the primary ultrasound image frames (labeled in FIG. 3 with 'P' annotations) having the imaging parameters designed for imaging a structure 130. In various embodiments, the primary ultrasound image frames 110 may be B-mode frames. In FIG. 3, the time 370 to acquire and/or process each primary frame is also shown below each frame. As illustrated, each primary frame 110 may take roughly twenty (20) milliseconds (ms) to acquire, and the resultant frame rate 375 would be roughly '50' frames per second (fps) (e.g., 1 second/20 ms per frame).

Figure 4:
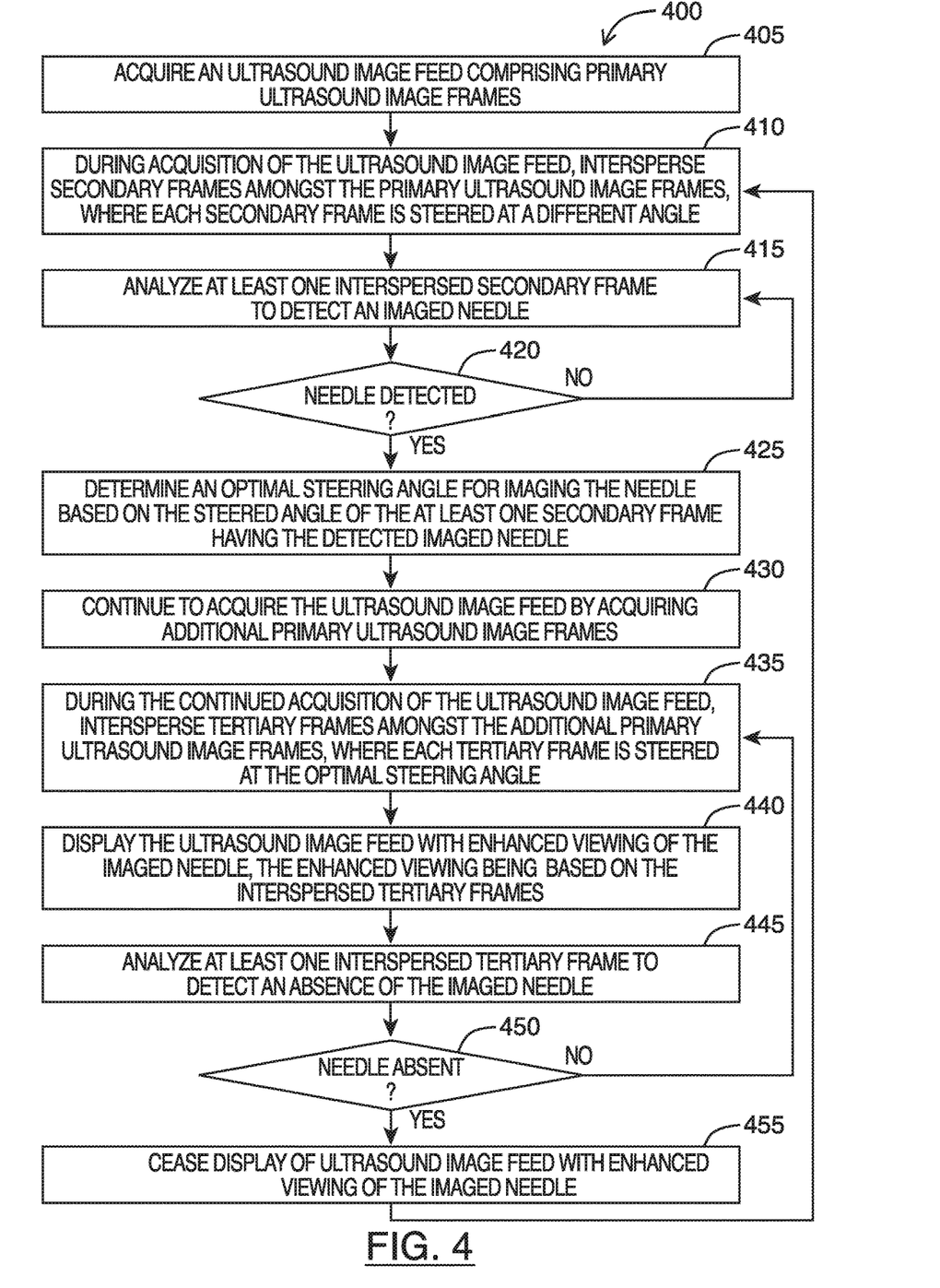
FIG. 4 is a flowchart diagram showing steps of a method for detecting and imaging a needle during ultrasound imaging, in accordance with at least one embodiment of the present invention.

Referring to FIG. 4, shown there generally as 400 is a flowchart diagram for a method of detecting and imaging a needle during ultrasound imaging, in accordance with at least one embodiment of the present invention. The method of FIG. 4 can generally be considered to have two phases: a survey phase for determining an optimal steering angle for imaging a needle (acts 410-425); and upon determining the optimal steering angle, a needle enhancement phase that provides enhanced viewing of the imaged needle while the needle remains present (acts 430-450). In discussing the method of FIG. 4, reference will also be simultaneously made to FIG. 5, which illustrates generally as 500 two series of frames for detecting and imaging a needle during ultrasound imaging, and associated frame rates, in accordance with at least one embodiment of the present invention. The first series of frames relate to the survey phase, and the second series of frames relate to the needle enhancement phase.

The method 400 of FIG. 4 may be performed by any suitable ultrasound machine or apparatus (e.g., such as is discussed below with respect to FIG. 6). For example, the method may be performed in an intervention procedure mode, which can be selected on the ultrasound machine.

At 405, an ultrasound image feed having primary ultrasound image frames 110 can be acquired. For example, these primary ultrasound image frames 110 may be a series of B-mode frames for imaging structures 130 in tissue, as was shown in FIG. 3. During acquisition of the ultrasound image feed, secondary frames can be interspersed amongst the primary ultrasound image frames 110, where each secondary frame is steered at a different angle (act 410).

Figure 5:
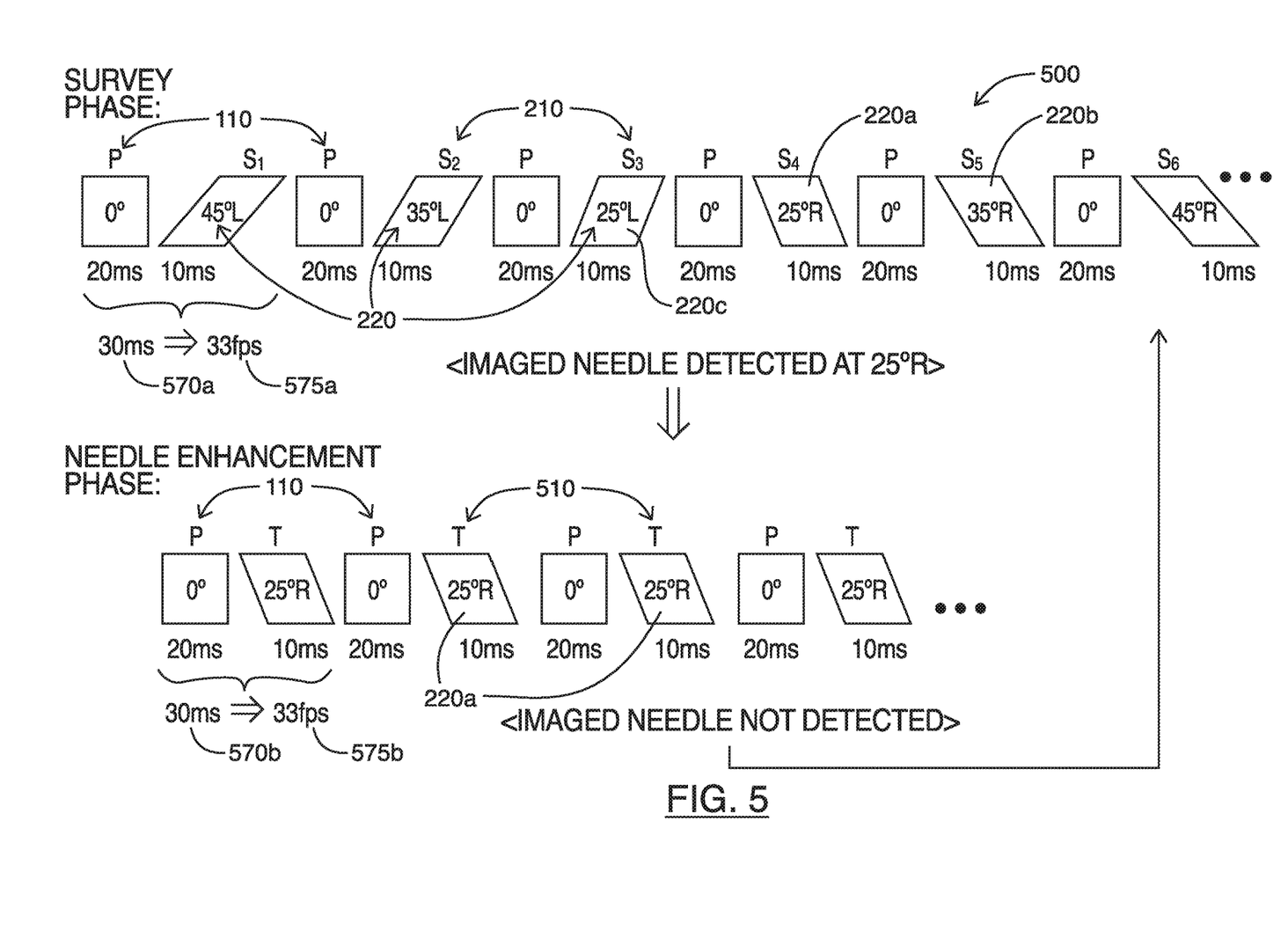
FIG. 5 shows a series of frames for detecting and imaging a needle during ultrasound imaging and associated frame rates, in accordance with at least one embodiment of the present invention.

Referring simultaneously to FIG. 5, shown in the first row is a series of frames where secondary frames 210 are interspersed amongst the primary ultrasound image frames 110 of an ultrasound image feed. As illustrated, the primary frames 110 (marked with a 'P' annotation above each frame) are unsteered, and are directed at an angle that is typical of a typical B-mode frame for a linear transducer (e.g., at zero degrees ('0°')).

Interspersed amongst these primary frames 110 are a number of secondary frames 210 (marked with a 'S' annotation above each frame). Each secondary frame $S_1$, $S_2$, $S_3$, $S_4$ . . . are steered at different respective angles 220. For example, secondary frame $S_1$ is steered at an angle of forty-five (45) degrees to the left of the normal direction of ultrasound signal travel (shown as '45° L' in FIG. 5); secondary frame $S_2$ is steered at '35° L'; and secondary frame $S_3$ is steered at '25° L'. Similarly, secondary frame $S_4$ is steered at an angle 220a of twenty-five degrees to the right of the normal direction of ultrasound signal travel (shown as '25° R' in FIG. 5); and secondary frame $S_5$ is steered at '35° R'.

At 415, the method may involve analyzing at least one secondary frame 210 of the interspersed secondary frames 210, to detect an imaged needle. For example, analysis of a steered secondary frame 210 may involve performing image analysis techniques on the at least one secondary frame 210. Any suitable image analysis technique for identifying an imaged needle may be used. Some example techniques include edge detection and/or straight line detection (e.g., including use of a Hough transform). In some embodiments, act 415 may involve performing the method described in Applicant's co-pending U.S. patent application Ser. No. 15/458,967 entitled "SYSTEMS AND METHODS FOR IDENTIFYING AN IMAGED NEEDLE IN AN ULTRASOUND IMAGE" filed herewith, issued as U.S. Pat. No. 10,102,452, the entire contents of which are hereby incorporated by reference.

If a needle is not detected (the 'NO' branch of act 420), the method may proceed back to act 415 to continue analyzing the interspersed secondary frames 210. However, if a needle is detected (the 'YES' branch at act 420), the method may proceed to act 425. In various embodiments, the condition for determining when an imaged needle has been detected at act 420 may vary. For example, in some embodiments, identification of an imaged needle in a single secondary frame 210 may result in a determination that an imaged needle has been detected. However, to provide enhanced confidence of the presence of the needle, the needle may not be considered detected at act 420 until a needle is determined to be imaged in at least 2 or more successive secondary frames 210.

At 425, upon detection of an imaged needle in the at least one secondary frame 210, the method involves determining an optimal steering angle for imaging the needle. The optimal steering angle may be based on the steered angle of the at least one secondary frame 210 having the detected imaged needle. For example, in embodiments where a needle is determined to be detected if the needle is identified in a single secondary frame 210, the optimal steering angle may be the steered angle 220 of such secondary frame 210. However, in embodiments where an imaged needle is not determined to be detected until it appears in two (2) or more successive secondary frames 210, the optimal steering angle may be determined by comparing the imaged needle in the secondary frames 210 in which the needle was identified. The optimal steering angle may then be selected to be the steering angle 220 of the secondary frame 210 with the optimal image of the needle.

When comparing amongst multiple secondary frames 210 to determine which secondary frame 210 has the optimal image of the needle, various factors may be taken into account. For example, if a confidence metric based on spatial image analysis techniques was used to determine the presence of an imaged needle (e.g., line brightness, straight line detection, and/or other suitable image analysis technique), a secondary frame having the highest confidence metric may be used to determine the secondary frame 210 that has the optimal image of the needle. Additionally or alternatively, if there is a threshold value for a given confidence metric, the amount to which the confidence metric value exceeds the threshold may be used to determine the secondary frame 210 that has the optimal image of the needle. The steered angle 220 of that secondary frame 210 may then be selected to be the optimal steering angle.

Once the optimal steering angle is determined, the method may proceed to act 430 and begin the needle enhancement phase. At 430, the method continues to acquire the ultrasound image feed by acquiring additional primary ultrasound image frames 110. At 435, during the continued acquisition of the ultrasound image feed, tertiary frames may be interspersed amongst the additional primary ultrasound image frames 110, where each tertiary frame is steered at the optimal steering angle. In some embodiments, the secondary frames 210 may continue to be interspersed amongst the primary ultrasound image frames 110 as the tertiary frames are also interspersed amongst the primary ultrasound image frames 110. However, to reduce the negative impact on frame rate, upon commencement of the interspersing of tertiary frames, the method may also cease the interspersing of secondary frames 210 in the ultrasound image feed.

Referring again to FIG. 5, shown there in the second row is a series of frames for the needle enhancement phase where tertiary frames 510 are interspersed amongst the primary ultrasound image frames 110 of an ultrasound image feed. As illustrated, the primary frames 110 (again marked with a 'P' annotation above each frame) remain unsteered (e.g., at zero degrees (0°)). However, interspersed amongst these frames are a number of tertiary frames 510 (marked with 'T' annotations above each frame). Each tertiary frame 510 is steered in the same angle 220a ('25° R') which, in the example embodiment, is the optimal steering angle detected at act 425. As illustrated in FIG. 5, the interspersing of the secondary frames 210 amongst the primary frames 110 has also ceased during the needle enhancement phase.

Referring back to FIG. 4, at 440, the ultrasound image feed may be displayed with enhanced viewing of the imaged needle and the enhanced viewing can be based on the interspersed tertiary frames 510. For example, the imaged needle in the tertiary frames 510 can be used to generate a mask highlighting the imaged needle, and the mask can then be combined with the primary image frames 110 in a manner that enhances the viewing of the imaged needle.

Referring still to FIG. 4, at 445, in some embodiments, during the continued acquisition of the ultrasound image feed, at least one tertiary frame 510 of the interspersed tertiary frames 510 may be analyzed to detect an absence of the imaged needle. For example, the image analysis discussed above at act 415 for the secondary frames 210 may now be performed on the tertiary frames 510 to confirm the imaged needle continues to be detected in each tertiary frame 510. For example, if an image analysis technique involving thresholding is used, a needle may be determined to be absent if the value being tested falls below a set threshold.

If the absence of a needle is not detected (the 'NO' branch at act 450), the method may continue back to acts 435-440 to continue interspersing tertiary frames 510 at the optimal steering angle 220a (e.g., as shown in FIG. 5) and displaying the ultrasound image feed with enhanced viewing of the imaged needle. However, if the needle is determined to be absent (the 'YES' branch at act 450), the display of the ultrasound image feed with enhanced viewing of the imaged needle may cease (act 455).

In various embodiments, the condition for determining when an imaged needle is absent at act 450 may vary. For example, image analysis of a single tertiary frame 510 may result in a needle failing to be identified (e.g., the needle being absent). However, due to the imaged needle potentially being moved into and out of the plane of the ultrasound imaging signals during an interventional procedure, it is possible that the absence of the needle is only temporary (e.g., the needle may be positioned back into plane and thus be viewable in subsequent tertiary frames 510). Thus, to provide enhanced confidence of the absence of the needle, the needle may not be considered absent at act 450 until the needle is determined to be not imaged in a number of successive tertiary frames 510 (e.g., at least ten (10) successive tertiary frames 510) and/or a period of time (e.g., one-third ($\frac{1}{3}$) of a second).

After act 455, the method may cycle back to act 410, where secondary frames 210 are interspersed amongst the primary ultrasound frames 110 and each secondary frame 210 is steered at different angles 220. The method may then continue to detect the presence of a needle as discussed above. In some embodiments, this may also involve ceasing the interspersing of tertiary frames 510 in the ultrasound image feed. Referring simultaneously to FIG. 5, it can be seen that if an imaged needle is not detected (e.g., determined to be absent), an arrow indicates that the method may revert back to the survey phase. As illustrated, the interspersing of the tertiary frames 510 has ceased, and the interspersing of secondary frames 210 in the ultrasound image feed is restored.

In various embodiments, acts 440 and 455 of FIG. 4 to respectively begin and cease display of the enhanced viewing of the imaged needle may be performed with visual effects. For example, when beginning the enhanced viewing of the imaged needle (e.g., with a colored highlighting or other marking), such highlighting may be introduced via a fade-in effect. Similarly, when ceasing to display the enhanced viewing of the needle, the highlighting may fade-out over a series of frames. In this manner, the beginning and ending of the enhanced viewing of the imaged needle may appear less abrupt for an ultrasound operator. As it may be challenging to position the needle for visualization because the needle may move into and out of the plane of ultrasound beam travel, the visual effect(s) (e.g., the needle intensity slowly decreasing or fading out) may provide visual feedback for an ultrasound operator (e.g., so as to move the needle back towards to the plane of ultrasound beam travel).

Referring still to FIG. 5, during the survey phase, the primary ultrasound image frames 110 can be acquired using a first set of imaging parameters, and the interspersed secondary frames 210 can be acquired using a second set of imaging parameters; with the second set of imaging parameters resulting in the interspersed secondary frames 210 having less image information than the primary ultrasound image frames 110. In one example embodiment, the primary ultrasound image frames 110 are standard B-mode frames having imaging parameters configured to achieve a high-quality image of tissue 130 (as shown in FIG. 1). For example, these imaging parameters may consist of a high dynamic range, low noise floor, Single Line Acquisition (SLA) and/or a high line density—imaging parameters that can result in a high resolution image with a substantial amount of image information.

However, the second set of imaging parameters used to generate the secondary frames 210 may be selected to generate frames with less image information. Since it is possible to perform needle detection on image frames with less image information than primary frames 110, reducing image information in a secondary frame 210 can reduce the processing loads required to process secondary image frames 210. For example, the second set of imaging parameters may have a lower dynamic range that requires fewer bits for storage and processing, and/or a higher noise floor that may results in sparser image data and thus lower processing.

Depending on the imaging parameters that are modified, the time required to acquire a secondary frame 210 may also be reduced. For example, and although this is not illustrated as between the ultrasound signals 120 in FIG. 1 and the ultrasound signals 120b in FIG. 2, another imaging parameter that may be different is the line density. By reducing the line density in the second set of imaging parameters versus the first set of imaging parameters, the computational load required to process the secondary frame 210 may further be reduced. Additionally, lowering the line density may reduce the transmit/receive times to acquire a secondary frame 210. This may further allow the time required to process a secondary frame 210 to be reduced.

Moreover, another imaging parameter that may additionally or alternatively be modified may be line acquisition per transmit event. As will be understood by persons skilled in the art, images generated using SLA techniques have a single receive scanline for a single transmitted ultrasound signal 110 and images generated using Multi-Line Acquisition (MLA) techniques have multiple receive scanlines for a single transmitted ultrasound signal 110. In various embodiments, the first set of imaging parameters used to acquire the primary ultrasound image frames 110 may use SLA techniques to provide improved lateral resolution. However, since high lateral resolution may not be necessary for identifying an optimal steering angle, the second set of imaging parameters used to acquire the secondary frames 210 can use MLA techniques to reduce the number of transmit events (and correspondingly, time) required to acquire a secondary frame 210. In turn, this may allow the overall frame rate to be increased.

Referring still to FIG. 5, noted below each primary frame 110 and secondary frame 210 are example times to acquire and process each frame 110, 210. As shown, a primary frame 110 may take '20 ms' for acquisition and processing using the first set of imaging parameters. However, due to the use of the second set of imaging parameters (e.g., with lower dynamic range, higher noise floor ratio, lower line density, and/or MLA) when generating the secondary frames 210, the time for acquiring and processing a secondary frame 210 can be reduced to '10 ms'. This may lower the overall time 570a required to generate a single frame for display on the ultrasound image feed during the survey phase to '30 ms'. Correspondingly, this may result in a frame rate of '33 fps' (1 second/30 ms per frame).

By selecting second imaging parameters in a manner that reduce the time required to acquire and/or process a secondary frame 210, the impact of interspersing secondary frames 210 amongst primary frames 110 may thus be reduced. In the example embodiment discussed, the frame rate is decreased from '50' fps in a regular imaging mode (e.g., as is shown in FIG. 3) to a frame rate that is still relatively high at above '30 fps'. In contrast, had the same imaging parameters been used for the secondary frames 210 as the primary frames 110, the acquisition and processing time for the secondary frames 210 would be the same '20 ms' and the overall time for acquiring and processing a frame to be displayed would be '40 ms'. This would result in a lower frame rate of '25 fps' (1 second/40 ms per frame). In various embodiments, depending on the imaging parameters used to acquire the secondary frames 210, the frame rate of the ultrasound image feed having the interspersed secondary frames 210 may potentially be even lower. For example, in some embodiments, the ultrasound image feed having the interspersed secondary frames 210 is maintained at least at ten (10) fps.

In the example discussed, the imaging parameters modified as between the secondary frames 210 and primary frames 110 include dynamic range, noise floor ratio, line acquisition per transmit event, and/or line density. However, in various embodiments, other imaging parameters may also be modified. For example, additional or alternative imaging parameters that may be modified include transmit frequency, receive frequency, and/or pulse width.

In some embodiments, these imaging parameters may be modified to improve detection of an imaged needle. For example, the second set of imaging parameters used to generate the secondary frames 210 may have a lower transmit frequency that results in ultrasound signals with lower attenuation (e.g., so that imaged needles at deeper depths may be located). Additionally or alternatively, the second set of imaging parameters may configure the parameters of the ultrasound pulse to have higher energy (e.g., by using a dual pulse) so as to create a stronger echo signal of the imaged needle. In turn, this may facilitate better detection of an imaged needle.

During the needle enhancement phase, the frame rate of the ultrasound image feed can be maintained. For example, in FIG. 5, the acquisition and processing time for the primary frames 110 will still be '20 ms'. However, the imaging parameters used to acquire the tertiary frames 510 can be configured to be similar to the second set of imaging parameters used for secondary frames 210. As illustrated in FIG. 5, this may result in the tertiary frames 510 also having an acquisition and processing time of '10 ms'. As a result, the overall time 570b to generate and display a frame in the needle enhancement phase is similar to that in the survey phase (e.g., '30 ms'). This results in a frame rate 575b of roughly '33 fps', which is similar to that discussed above in the survey phase. In this manner, the frame rate as between the needle enhancement phase and the survey phase can generally be kept similar so that there is no perceived difference in imaging by an ultrasound operator when a needle is detected and when the absence of the needle is detected.

As noted above, during the needle enhancement phase, at act 450, it is possible to configure the needle to not be considered absent until the needle is determined to be not imaged in a number of successive tertiary frames 510. In the illustrated embodiment where the overall time for generating a frame 570b is '30 ms', using a parameter of ten (10) successive tertiary frames 510 to confirm absence of a needle may allow roughly '300 ms' (10×'30 ms') or roughly ⅓ of a second for allowing the needle to move in and out of plane of the ultrasound signals before having the enhanced viewing of the image needle in the ultrasound image feed be stopped. In some embodiments, this number can be greater ten (10). For example, in some embodiments, the number can be thirty (30) successive tertiary frames 510; which may allow roughly '900 ms' (30×'30 ms') or roughly almost a second for allowing the needle to move in and out of plane. This number of successive tertiary frames 510 may differ in various embodiments.

In certain embodiments, the needle may not be considered absent until the needle is determined to be not imaged after a period of time (e.g., in addition or alternative to a number of successive tertiary frames 510). In some embodiments, this period of time may be at least ⅓ of a second. In some embodiments, this period of time may be approximately 1000 ms (e.g., 1 second).

In FIG. 5, the interspersing of secondary frames 210 and tertiary frames 510 respectively is performed by interleaving such frames between successive primary ultrasound image frames 110. However, in various embodiments, the interspersing may take different forms. For example, in some embodiments, the interspersing of these frames 210, 510 amongst the primary frames 110 may involve inserting a frame 210, 510 every 'N' primary frames 110, where 'N' is any integer value. In some embodiments, the frames 210, 510 may be interspersed less frequently to allow for a higher frame rate. However, doing so may result in slower response times for when an imaged needle is determined to be detected or absent. The embodiment illustrated in FIG. 5 where the frames 210, 510 are interleaved between primary frames 110 may allow for enhanced detection responsiveness.

As shown in FIG. 5, the primary ultrasound image frames 110 are acquired by sequentially transmitting ultrasound signals in a direction that is normal to the transducer head (e.g., as is typical for the example linear transducer shown). However, the secondary frames 210 during the survey phase can be steered on both sides of this normal direction. Whereas some traditional systems require user input to select which side of the transducer a needle will be inserted on, the present embodiments may allow the secondary frames 210 to be steered at various angles on either side of the normal direction of ultrasound signal travel. By interspersing these various steered secondary frames 210 in the manner discussed herein, it is possible to direct the secondary frames 210 on both sides of the transducer without significantly degrading the frame rate. In this manner, the present embodiments may detect an imaged needle when it is inserted on either side of the transducer, while still maintaining an acceptable frame rate for imaging the structures 130.

In various embodiments, the angle 220 (as shown in FIG. 2) at which the secondary frames 210 are steered may vary. For example, in some embodiments, the primary ultrasound image frames 110 may be acquired by transmitting ultrasound signals in a direction (e.g., perpendicular to the transducer head), and the interspersed secondary frames 210 may be steered at angles 220 between ten (10) and sixty (60) degrees from that direction on either or both sides of such direction. The incremental change in angles between successive secondary frames 210 may also vary. For example, in some embodiments, each successive secondary frame 210 may be steered at increments of between 5 to 20 degrees.

Having larger steered angles 220 may allow needles that are inserted at steep angles to be detected. However, having too large a range of angles 220 for the secondary frames 220 may potentially increase the number of secondary frames 210 required to perform a full sweep from the leftmost largest angle 220 to the rightmost largest 220. In turn, this may result in reduced needle detection responsiveness during the survey phase.

In various embodiments, these different parameters may be configured to achieve a desired optimal needle detection angle and/or needle detection responsiveness. For example, in the embodiment of FIG. 5, three secondary frames 210 are steered at 10 degree increments from 45 degrees to 25 degrees on each side of the normal direction of ultrasound signal travel. However, in other embodiments, the range of angles on either or both sides of the ultrasound signals and/or the incremental changes in angles 220 may differ.

For example, in some embodiments, there may be two secondary frames 210 steered at 40° and 20° on each side (e.g., the incremental angle difference being 20°). This would reduce the range of angles 220 for the secondary frames, and also the number of secondary frames 210 needed to perform a full sweep. In turn, this may also reduce the overall time required to do a full sweep, and thus may enhance needle detection responsiveness. However, such a configuration may also result in the optimal steering angle ultimately chosen being potentially less accurate because of the reduced granularity of steered angle coverage.

Conversely, it is possible to increase the number of range of angles 220 and/or decrease the incremental change in the angle 220 of successive secondary frames 210. For example, in some embodiments, it may be possible to have four secondary frames 210 steered at 50°, 40°, 30°, and 20° on each side of the transducer. This configuration has a larger range of angles 220 and a smaller incremental change in the angle 220 of successive secondary frames 210. This may allow the optimal steering angle 220 ultimately chosen for the needle enhancement phase to be more accurate. However, this accuracy may require more secondary frames 210 to perform a full sweep across all the angles 220, and thus may reduce needle detection responsiveness. The configurations discussed herein are for illustration only, and other configurations may be possible in other embodiments. The present embodiments encompass any configuration of these various parameters.

By interspersing secondary frames 210 steered at various angles during the survey phase, and locking into an optimal steering angle upon detection of an imaged needle, the present embodiments may allow for automated detection and optimal imaging of inserted needles without significant decrease in frame rate. Also, by configuring the imaging parameters of the interspersed secondary frames 210 and tertiary frames 510 to generate less image information, the impact of the interspersed frames on frame rate can be further minimized. Since the sequence of ultrasound signals used to perform ultrasound imaging are changed based on real-time image analysis, the methods described herein may also be considered a method of dynamically modifying ultrasound sequencing.

As discussed above, some traditional solutions to poor imaging of a needle is to use echogenically-enhanced needles; which add cost and require a change in the workflow of a medical professional. In contrast, the enhanced viewing of an imaged needle discussed herein may be achieved on regular needles that are not configured for enhanced echogenicity.

Figure 6:
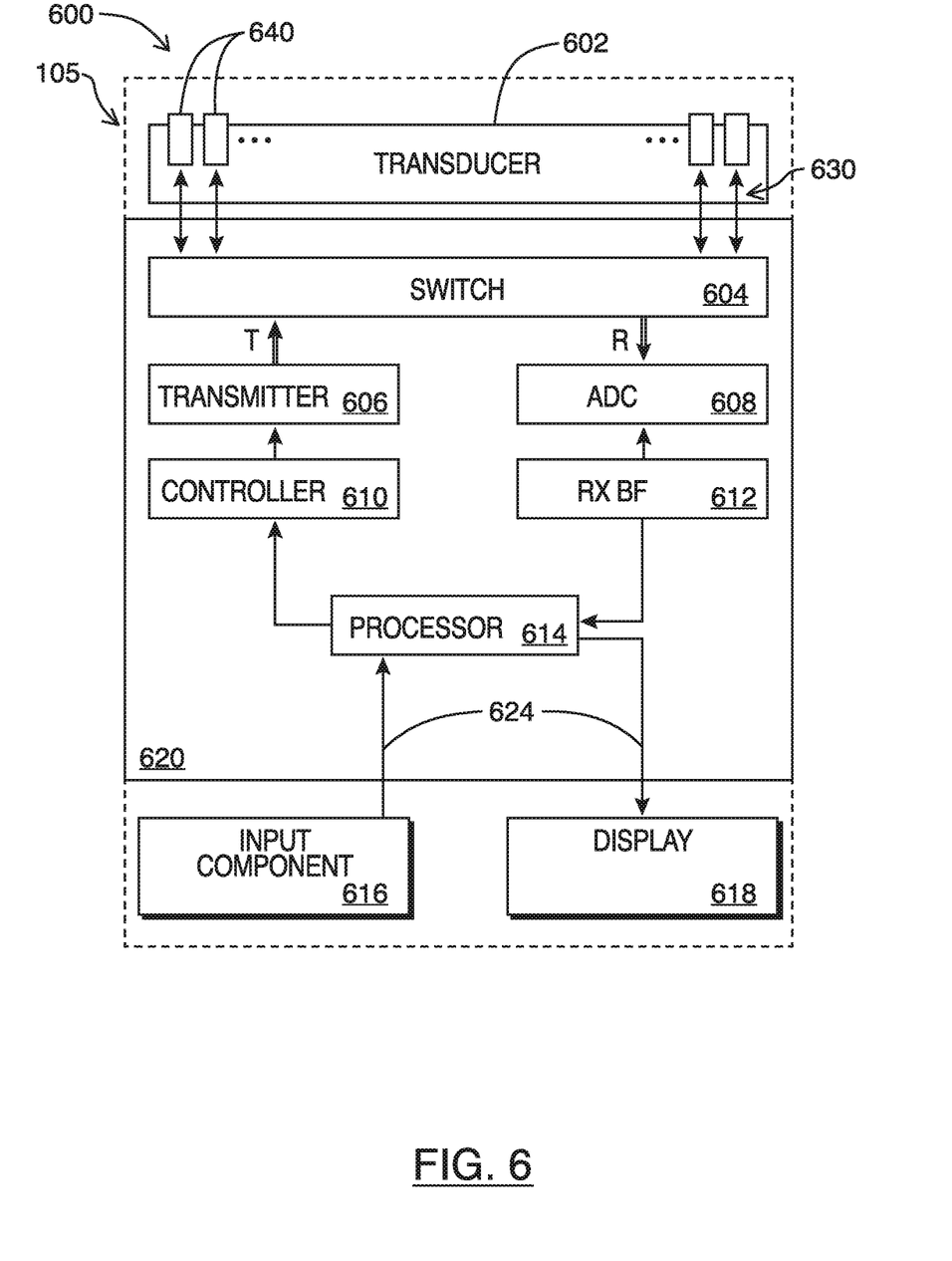
FIG. 6 shows a functional block diagram of an ultrasound system, in accordance with at least one embodiment of the present invention.

Referring to FIG. 6, shown there generally as 600 is a functional block diagram of an ultrasound system, in accordance with at least one embodiment of the present invention. The ultrasound machine 600 may include a transducer head 105 discussed above in relation to FIG. 1. The transducer head 105 may include a transducer array 602 with a number of constituent transducer elements 640.

A transmitter 606 may be provided to energize the transducer elements 640 to produce the ultrasound signals 120 (as shown in FIG. 1). Another group of transducer elements 640 may then form the receive aperture to convert the received echo ultrasound energy into analog electrical signals which are then sent through a set of transmit/receive (T/R) switches 604 to a number of channels of echo data. A set of analog-to-digital converters (ADCs) 608 digitises the analog signals from the switches 604. The digitised signals are then sent to a receive beamformer 612.

Transmitter 606 and receive beamformer 612 are operated under the control of a scan controller 610. Receive beamformer 612 combines the separate echo signals from each channel using pre-calculated time delay and weight values to yield a single echo signal which represents the received energy from a particular scanline. Under the direction of the scan controller 610, the ultrasound machine 600 generates and processes additional transmit and receive events to produce the multiple scanlines required to form an ultrasound image. Ultrasound images are typically made up of fifty (50) to a few hundred lines. Typically, the number of scanlines of an ultrasound image generated from a sequential transducer such as discussed herein may correspond to the number of transducer elements 640 in the transducer array 602. As discussed above, the scan line density may vary between primary ultrasound frames 110 used for imaging tissue structures 130 and secondary/tertiary ultrasound frames 210, 510 used for needle detection and imaging.

An ultrasound processor 614 may be in communication with the receive beamformer 612 and applies the necessary processing steps to combine multiple scanlines from these different transmit events to yield image data. The processor 614 communicates this image data via a data link 624 to a display device 618. Data link 624 may include a cable, a wireless connection, or the like. Display device 618 displays the ultrasound image to the user. In some embodiments, the display device 618 may not be separate, and instead be provided as an integrated part of the ultrasound machine 600. In the latter case, the data link 624 may be a data bus or other suitable connector between the processor 614 and the display 618.

The input component 616 may receive input to operate the ultrasound machine 600. For example, the input component 616 may be used to receive input that begins operation of an intervention procedure mode. The intervention procedure mode may involve performing the method of FIG. 4 discussed herein. The input component 616 may be provided in the form of any physical or software-based user interface control. In some embodiments, a user control such as a push button, a graphical user interface control, or the like may be operated by an ultrasound operator. The data input initiating performance of the methods described herein can be provided to ultrasound processor 614 via data link 624. In turn, the ultrasound processor 614 may provide a configuration signal to controller 610 to initiate interspersing of secondary frames 210 amongst the primary frames 110 of the ultrasound image feed being generated. The method in FIG. 4 discuss herein may then be performed to detect and enhance viewing of an imaged needle.

As discussed above, input may not be required to switch between the survey phase and the needle enhancement phase during the performance of the method of FIG. 4. Instead, the method of FIG. 4 may continue to alternate between these two phases until a user provides further input via input component 616 to exit operation of the intervention procedure mode. Upon receiving such input, the ultrasound machine 600 may cease interspersing either secondary frames 210 and/or tertiary frames 510 amongst the primary frames 110 of the ultrasound image feed, and return to a regular imaging mode (or other previous imaging mode previous to the selection of the intervention procedure mode).

The embodiments described herein may be used with ultrasound machines 600 having a variety of different form factors. As illustrated in FIG. 6, the transducer head 105 is shown in dotted outline in relation to the processing components 620 of the ultrasound machine 600 to illustrate that it can be coupled thereto via any type of communication link 630. For example, in some embodiments, the transducer may be detachably coupled to the body of the ultrasound machine 600 via a cable or other suitable wired connection. In some such embodiments, the ultrasound machine 600 may include both the processing components and the display 618 and input component 616 in a unitary body.

In certain embodiments, the transducer head 105 and processing components 620 may be provided in a single device (e.g., having a unitary body). In such case, the processor 614 may communicate to display 618 and input component 616 via a wireless communication link. The input component 616 and display 618 is shown in dotted outline to show that they may not form part of the processing components 620 in such embodiments. In some such embodiments, the single device containing the transducer head 105 and processing components 620 may be provided as a wireless handheld probe that is configured to communicate with an external wireless computing device containing a display 618 and is able to provide the image component 616 (e.g., a touchscreen). In some embodiments, such wireless handheld probe may be provided in a form factor that has a mass that is less than 4.5 kilograms.

While a number of exemplary aspects and embodiments have been discussed above, those of skill in the art will recognize that may be certain modifications, permutations, additions and sub-combinations thereof. While the above description contains many details of example embodiments, these should not be construed as essential limitations on the scope of any embodiment. Many other ramifications and variations are possible within the teachings of the various embodiments.

Interpretation of Terms

Unless the context clearly requires otherwise, throughout the description and the claims:
- "comprise", "comprising", and the like are to be construed in an inclusive sense, as opposed to an exclusive or exhaustive sense; that is to say, in the sense of "including, but not limited to";
- "connected", "coupled", or any variant thereof, means any connection or coupling, either direct or indirect, between two or more elements; the coupling or connection between the elements can be physical, logical, or a combination thereof;
- "herein", "above", "below", and words of similar import, when used to describe this specification, shall refer to this specification as a whole, and not to any particular portions of this specification;
- "or", in reference to a list of two or more items, covers all of the following interpretations of the word: any of the items in the list, all of the items in the list, and any combination of the items in the list;
- the singular forms "a", "an", and "the" also include the meaning of any appropriate plural forms.

Unless the context clearly requires otherwise, throughout the description and the claims:

Words that indicate directions such as "vertical", "transverse", "horizontal", "upward", "downward", "forward", "backward", "inward", "outward", "vertical", "transverse", "left", "right", "front", "back", "top", "bottom", "below", "above", "under", and the like, used in this description and any accompanying claims (where present), depend on the specific orientation of the apparatus described and illustrated. The subject matter described herein may assume various alternative orientations. Accordingly, these directional terms are not strictly defined and should not be interpreted narrowly.

Embodiments of the invention may be implemented using specifically designed hardware, configurable hardware, programmable data processors configured by the provision of software (which may optionally comprise "firmware") capable of executing on the data processors, special purpose computers or data processors that are specifically programmed, configured, or constructed to perform one or more steps in a method as explained in detail herein and/or combinations of two or more of these. Examples of specifically designed hardware are: logic circuits, application-specific integrated circuits ("ASICs"), large scale integrated circuits ("LSIs"), very large scale integrated circuits ("VLSIs"), and the like. Examples of configurable hardware are: one or more programmable logic devices such as programmable array logic ("PALs"), programmable logic arrays ("PLAs"), and field programmable gate arrays ("FPGAs"). Examples of programmable data processors are: microprocessors, digital signal processors ("DSPs"), embedded processors, graphics processors, math co-processors, general purpose computers, server computers, cloud computers, mainframe computers, computer workstations, and the like. For example, one or more data processors in a control circuit for a device may implement methods as described herein by executing software instructions in a program memory accessible to the processors.

For example, while processes or blocks are presented in a given order herein, alternative examples may perform routines having steps, or employ systems having blocks, in a different order, and some processes or blocks may be deleted, moved, added, subdivided, combined, and/or modified to provide alternative or subcombinations. Each of these processes or blocks may be implemented in a variety of different ways. Also, while processes or blocks are at times shown as being performed in series, these processes or blocks may instead be performed in parallel, or may be performed at different times.

The invention may also be provided in the form of a program product. The program product may comprise any non-transitory medium which carries a set of computer-readable instructions which, when executed by a data processor (e.g., in a controller and/or ultrasound processor in an ultrasound machine), cause the data processor to execute a method of the invention. Program products according to the invention may be in any of a wide variety of forms. The program product may comprise, for example, non-transitory media such as magnetic data storage media including floppy diskettes, hard disk drives, optical data storage media including CD ROMs, DVDs, electronic data storage media including ROMs, flash RAM, EPROMs, hardwired or pre-programmed chips (e.g., EEPROM semiconductor chips), nanotechnology memory, or the like. The computer-readable signals on the program product may optionally be compressed or encrypted.

Where a component (e.g. a software module, processor, assembly, device, circuit, etc.) is referred to above, unless otherwise indicated, reference to that component (including a reference to a "means") should be interpreted as including as equivalents of that component any component which performs the function of the described component (i.e., that is functionally equivalent), including components which are not structurally equivalent to the disclosed structure which performs the function in the illustrated exemplary embodiments of the invention.

Specific examples of systems, methods and apparatus have been described herein for purposes of illustration. These are only examples. The technology provided herein can be applied to systems other than the example systems described above. Many alterations, modifications, additions, omissions, and permutations are possible within the practice of this invention. This invention includes variations on described embodiments that would be apparent to the skilled addressee, including variations obtained by: replacing features, elements and/or acts with equivalent features, elements and/or acts; mixing and matching of features, elements and/or acts from different embodiments; combining features, elements and/or acts from embodiments as described herein with features, elements and/or acts of other technology; and/or omitting combining features, elements and/or acts from described embodiments.

It is therefore intended that the following appended claims and claims hereafter introduced are interpreted to include all such modifications, permutations, additions, omissions, and sub-combinations as may reasonably be inferred. The scope of the claims should not be limited by the preferred embodiments set forth in the examples, but should be given the broadest interpretation consistent with the description as a whole.

What is claimed is:

1. A method of ultrasound imaging, the method comprising:
    acquiring an ultrasound image feed, the ultrasound image feed comprising non-steered primary ultrasound image frames;
    during acquisition of the ultrasound image feed,
        interleaving steered secondary frames amongst the non-steered primary ultrasound image frames, wherein each steered secondary frame is steered at a different angle;
        analyzing at least one steered secondary frame, of the interleaved steered secondary frames, to detect an imaged needle;
        displaying the ultrasound image feed, wherein a frame of the ultrasound image feed is displayed after a single non-steered primary ultrasound image frame and a single steered secondary frame, so that the ultrasound image feed is maintained at a first frame rate;
        upon detection of an imaged needle in the at least one steered secondary frame, determining an optimal steering angle for imaging the needle, the optimal steering angle being based on the steered angle of the at least one steered secondary frame having the detected imaged needle;
    continuing to acquire the ultrasound image feed by acquiring additional non-steered primary ultrasound image frames;
    during the continued acquisition of the ultrasound image feed,
        ceasing the interleaving of the steered secondary frames amongst the non-steered primary ultrasound image frames;
        interleaving steered tertiary frames amongst the additional non-steered primary ultrasound image frames, wherein each steered tertiary frame is steered at the optimal steering angle and is combined with one of the additional non-steered primary ultrasound image frames to generate an ultrasound image frame with enhanced viewing of the imaged needle; and displaying the ultrasound image feed with enhanced viewing of the imaged needle, the ultrasound image feed comprising the generated ultrasound image frames with enhanced viewing of the imaged needle, wherein a frame of the ultrasound image feed with enhanced viewing of the imaged needle is displayed after a single non-steered primary ultrasound image frame and a single steered tertiary frame, so that the ultrasound image feed with enhanced viewing of the imaged needle is maintained at a second frame rate that is substantially similar to the first frame rate.

2. The method of claim 1, wherein during the continued acquisition of the non-steered primary ultrasound image frames of the ultrasound image feed, the method further comprises:

continuing to acquire additional interleaved steered tertiary frames;

analyzing at least one additional steered tertiary frame, of the additional interleaved steered tertiary frames, to detect an absence of the imaged needle; and upon detection of the absence of the imaged needle in the at least one additional steered tertiary frame, ceasing the interleaving of additional steered tertiary frames amongst the additional non-steered primary ultrasound image frames;

ceasing the display of the ultrasound image feed with enhanced viewing of the imaged needle; and restoring the interleaving of steered secondary frames amongst the non-steered primary ultrasound image frames.

3. The method of claim 1, wherein the first frame rate of the ultrasound image feed, having the interleaved steered secondary frames amongst the non-steered primary ultrasound image frames, is maintained at least at 10 frames per second (fps).

4. The method of claim 3, wherein the non-steered primary ultrasound image frames are acquired using a first set of imaging parameters, and the interleaved steered secondary frames are acquired using a second set of imaging parameters; and wherein the second set of imaging parameters result in the interleaved steered secondary frames having less image information than the non-steered primary ultrasound image frames.

5. The method of claim 4, wherein the imaging parameters that are different between the first set of imaging parameters and the second set of imaging parameters is selected from a group consisting of: noise floor ratio, dynamic range, transmit frequency, receive frequency, line acquisition per transmit event, line density, or pulse width.

6. The method of claim 3, wherein the non-steered primary ultrasound image frames are acquired by transmitting ultrasound signals in a direction, and the interleaved steered secondary frames are steered on both sides of the direction.

7. The method of claim 3, wherein the non-steered primary ultrasound image frames are acquired by transmitting ultrasound signals in a direction, and the interleaved steered secondary frames are steered at angles between 10 and 60 degrees from the direction.

8. The method of claim 3, wherein the interleaved steered secondary frames are successively steered in at least 5 degree increments.

9. The method of claim 3, wherein the interleaved steered secondary frames are successively steered in increments of no greater than 20 degrees.

10. The method of claim 3, wherein when analyzing the at least one steered secondary frame, the needle is considered detected if the needle is determined to be imaged in at least 2 successive steered secondary frames.

11. The method of claim 10, wherein the optimal steering angle is determined by comparing the imaged needle in the at least 2 successive steered secondary frames, and selecting the steered angle of the steered secondary frame having the optimal imaged needle.

12. The method of claim 2, wherein when analyzing the at least one additional steered tertiary frame, the needle is considered absent if the needle is determined to be not imaged in 10 to 30 successive additional steered tertiary frames.

13. The method of claim 2, wherein when analyzing the at least one additional steered tertiary frame, the needle is considered absent if the needle is absent for between ⅓ of a second and 1 second.

14. The method of claim 3, wherein the needle comprises a needle not configured for enhanced echogenicity.

15. An ultrasound imaging apparatus comprising:

a processor; and a memory storing instructions for execution by the processor, wherein when the instructions are executed by the processor, the processor is configured to:

acquire an ultrasound image feed, the ultrasound image feed comprising non-steered primary ultrasound image frames;

during acquisition of the ultrasound image feed, interleave steered secondary frames amongst the non-steered primary ultrasound image frames, wherein each steered secondary frame is steered at a different angle;

analyze at least one steered secondary frame, of the interleaved steered secondary frames, to detect an imaged needle;

display the ultrasound image feed, wherein a frame of the ultrasound image feed is displayed after a single non-steered primary ultrasound image frame and a single steered secondary frame, so that the ultrasound image feed is maintained at a first frame rate;

upon detection of an imaged needle in the at least one steered secondary frame, determine an optimal steering angle for imaging the needle, the optimal steering angle being based on the steered angle of the at least one steered secondary frame having the detected imaged needle;

continue to acquire the ultrasound image feed by acquiring additional non-steered primary ultrasound image frames;

during the continued acquisition of the ultrasound image feed, cease the interleaving of the steered secondary frames amongst the non-steered primary ultrasound image frames;

interleave steered tertiary frames amongst the additional non-steered primary ultrasound image frames, wherein each steered tertiary frame is steered at the optimal steering angle and is combined with one of the additional non-steered primary ultrasound image frames to generate an ultrasound image frame with enhanced viewing of the imaged needle; and display the ultrasound image feed with enhanced viewing of the imaged needle, the ultrasound image feed comprising the generated ultrasound image frames with enhanced viewing of the imaged needle, wherein a frame of the ultrasound image feed with enhanced viewing of the imaged needle is displayed after a single non-steered primary ultrasound image frame and a single steered tertiary frame, so that the ultrasound image feed with enhanced viewing of the imaged needle is maintained at a second frame rate that is substantially similar to the first frame rate.

16. A non-transitory computer readable medium storing instructions for execution by a processor of an ultrasound imaging apparatus, wherein when the instructions are executed by the processor, the processor is configured to:
   acquire an ultrasound image feed, the ultrasound image feed comprising non-steered primary ultrasound image frames;
   during acquisition of the ultrasound image feed,
      interleave steered secondary frames amongst the non-steered primary ultrasound image frames, wherein each steered secondary frame is steered at a different angle;
      analyze at least one steered secondary frame, of the interleaved steered secondary frames, to detect an imaged needle;
      display the ultrasound image feed, wherein a frame of the ultrasound image feed is displayed after a single non-steered primary ultrasound image frame and a single steered secondary frame, so that the ultrasound image feed is maintained at a first frame rate;
      detection of an imaged needle in the at least one steered secondary frame, determine an optimal steering angle for imaging the needle, the optimal steering angle being based on the steered angle of the at least one steered secondary frame having the detected imaged needle;
   continue to acquire the ultrasound image feed by acquiring additional non-steered primary ultrasound image frames;
   during the continued acquisition of the ultrasound image feed,
      cease the interleaving of the steered secondary frames amongst the non-steered primary ultrasound image frames;
      interleave steered tertiary frames amongst the additional non-steered primary ultrasound image frames, wherein each steered tertiary frame is steered at the optimal steering angle and is combined with one of the additional non-steered primary ultrasound image frames to generate an ultrasound image frame with enhanced viewing of the imaged needle; and
      display the ultrasound image feed with enhanced viewing of the imaged needle, the ultrasound image feed comprising the generated ultrasound image frames with enhanced viewing of the imaged needle, wherein a frame of the ultrasound image feed with enhanced viewing of the imaged needle is displayed after a single non-steered primary ultrasound image frame and a single steered tertiary frame, so that the ultrasound image feed with enhanced viewing of the imaged needle is maintained at a second frame rate that is substantially similar to the first frame rate.

* * * * *